United States Patent [19]

Gander et al.

[11] 4,375,461

[45] Mar. 1, 1983

[54] SULFONATED VINYL AROMATIC HOMOPOLYMERS AND COPOLYMERS AS DENTAL PLAQUE BARRIERS

[75] Inventors: Robert J. Gander, Whitehouse; Tibor Sipos, Lebanon; Carl J. Buck, Berkeley Heights, all of N.J.

[73] Assignee: Johnson & Johnson Products, Inc., New Brunswick, N.J.

[21] Appl. No.: 172,491

[22] Filed: Jul. 25, 1980

[51] Int. Cl.³ ............... A61K 7/16; A61K 7/22; A61K 31/315; A61K 31/205

[52] U.S. Cl. .................. 424/56; 424/54; 424/78; 424/289; 424/315; 424/316

[58] Field of Search ............... 424/48–52, 424/78, 315, 54, 56, 289, 316, 317

[56] References Cited

U.S. PATENT DOCUMENTS

| | | | |
|---|---|---|---|
| 3,072,619 | 1/1963 | Turbak | 260/79.3 |
| 3,385,905 | 5/1968 | Smith et al. | 260/505 R |
| 3,642,728 | 2/1972 | Canter | 260/79.3 |
| 3,862,309 | 1/1975 | Krochock | 424/78 |
| 4,096,089 | 6/1978 | Shibe et al. | 260/505 R |

FOREIGN PATENT DOCUMENTS

WO79/00456  7/1979  PCT Int'l Appl.

OTHER PUBLICATIONS

Zeitschrift für Physikalische Chemie Neue. Folge Bd. 56, S. 218–222 (1967)–Skerjanc et al.

*Primary Examiner*—Douglas W. Robinson

[57] ABSTRACT

Compositions and methods for preventing the attachment of dental plaque to the surfaces of the teeth of mammals comprise certain sulfonated vinylaromatic homopolymers and copolymers and the pharmaceutically acceptable salts thereof in a pharmaceutically acceptable vehicle, and the periodic application thereof to teeth.

7 Claims, No Drawings

SULFONATED VINYL AROMATIC HOMOPOLYMERS AND COPOLYMERS AS DENTAL PLAQUE BARRIERS

TECHNICAL FIELD

This invention relates to oral hygiene compositions and methods using such compositions to prevent attachment of bacteria to teeth. More particularly it relates to certain sulfonated polymeric materals that have been found useful in inhibiting the agglutination of oral microbes on teeth.

BACKGROUND ART

The prevention of the deposition of dental plaque on teeth is a highly desired result. Dental plaque results when cariogenic bacteria aggregate in colonies on the surface of teeth and form a tenacious deposit thereon. The presence of plaque on teeth is believed to be a precursor to development of dental caries and periodontal disease.

While many attempts have been made to control the effects of cariogenic bacteria and the dental plaque they produce, for example, by fluoride, flossing, brushing, etc., treatments, these are typically directed to either counteracting the secondary effects of plaque on the teeth and gums, or to the removal of plaque that is already formed on and adhering to the teeth and surrounding tissue. Such treatments are not, however, entirely successful, and must be supplemented with periodic treatment by dental professionals. To date, there is no commercially feasible home treatment method for preventing the formation of plaque or its adhesion to teeth.

THE INVENTION

A number of hydrophilic sulfonic acid and sulfonic acid salt derivatives of certain vinylaromatic homopolymers and copolymers have been synthesized and found to inhibit the deposition of dental plaque onto human teeth. These hydrophilic polymeric sulfonates have good film forming characteristics and, accordingly, are applied to teeth from various dentifrice formulations, mouth rinses, or other oral hygiene procedures. The sulfonated polymers of this invention are anionic in nature and substantially soluble in water or water/organic solvent vehicles, primarily because of the relatively high degree of sulfonation achieved during preparation of these derivatives. While the mechanism of action of the hydrophilic polymeric films in retarding plaque deposition is not known with absolute certainty, it is presumed that the films of anionically-charged polymers deposited on teeth effect a mutual repulsion between the negatively charged polymer film and the negatively charged microorganisms in oral fluids responsible for plaque generation. For example, when powdered human dental enamel was dispersed in the aqueous media containing salts of the polymeric sulfonates, a substantially negative surface charge was imparted to the enamel particles, as determined by zeta potential measurements. The sulfonated vinylaromatic polymers of this invention are especially effective as components of dentifrices and other oral hygiene preparations in reducing dental plaque deposition on teeth.

Hydrophilic, polymeric, anionic sulfonates useful for dental plaque control in accordance with the present invention are essentially sulfonated homopolymers of both unsubstituted and substituted styrene, 1-vinylnaphthalene, 2-vinylnaphthalene, and acenaphthylene, and certain copolymers thereof. These polymers may be prepared by several different synthetic methods, to be discussed hereinafter in greater detail, wherein the sulfonated derivatives are prepared by either (1) direct aromatic sulfonation of the aforementioned vinylaromatic homopolymers or copolymers, (2) free radical homopolymerization or copolymerization of sulfonic acid or sulfonic acid salt-substituted vinylaromatic monomers, or (3) chemical modification of certain chloromethyl ($CH_2Cl$)-substituted vinylaromatic monomers or polymers. The sulfonic acid derivatives are rendered even more hydrophilic and water soluble by conversion to metal salts of certain of the group IA alkali metals, Group IIA, IIB, and IIIA multivalent metals, or to ammonium or amine salts.

The sulfonated homopolymers and copolymers of this invention comprise at least 50% by weight of at least one repeating unit selected from the group consisting of structure (A),

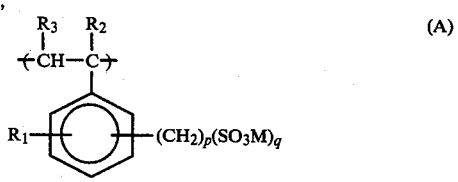

structure (B),

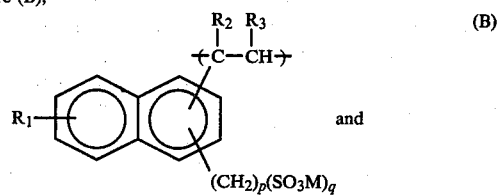

and structure (C),

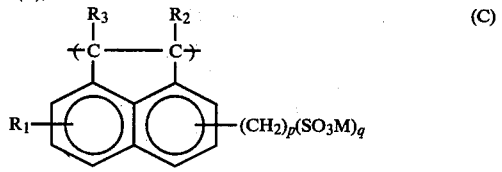

and from 0 to 50% by weight of a repeating unit selected from the group consisting of structure (D),

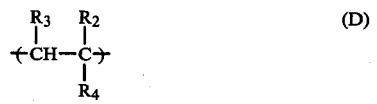

and structure (E),

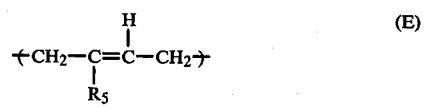

wherein $R_1$ is selected from the group consisting of hydrogen, linear or branched lower alkyl of up to 5 carbon atoms, alkoxy of 1–20 carbon atoms, or halogen, such as fluorine, chlorine, and bromine; $R_2$ and $R_3$ are each independently selected from the group consisting of hydrogen and methyl; $R_4$ is hydrogen or an alkyl group of 1–18 carbon atoms; and $R_5$ is selected from the group consisting of hydrogen, methyl, chlorine, bromine, and phenyl. Depending on the synthetic process utilized for the synthesis of the sulfonated polymers of this invention, q can range from 0.3 to 2.6 and p is either zero or a number equal to the value of q. M is either a metal ion such as lithium, sodium, potassium, calcium, magnesium, zinc, or aluminum, or hydrogen or an ammonium salt derived from ammonia or a pharmaceutically acceptable organic amine. The zinc salts are particularly preferred, since they generally exhibit higher substantivity to human dental enamel (after repeated washings with water) than the alkali metal salts. Significant reduction of plaque deposition is obtained when q is at least about 0.3 for polymers wherein the repeating units have only structure (A) repeating units. Similarly, significant efficacy is obtained when q is at least about 0.5 for polymers wherein the repeating units have structures (B) or (C). For copolymers having a substantial percentage of unsulfonated repeating units of structures D and E, the minimum efficacious q values are increased by the factor:

$$\frac{\text{moles }[(A) + (B) + (C) + (D) + (E)]}{\text{moles }[(A) + (B) + (C)]}$$

This factor corresponds to the inverse of the mole fraction of the aromatic repeating units in the copolymer.

The monomers and polymers required as building blocks for the synthesis of the sulfonated derivatives of the homopolymers and copolymers of this invention, comprising repeating units described previously as structures (A), (B), (C), (D), and (E), are generally available from chemical supply houses or can be synthesized by general organic reaction processes well known to those skilled in the art. Monomers used for synthesis of the sulfonated vinylaromatic homopolymers and copolymers of this invention are represented by the generalized structures (F) through (M),

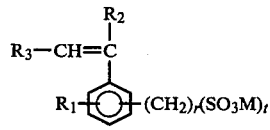
(F)

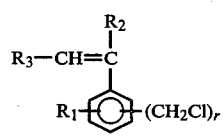
(G)

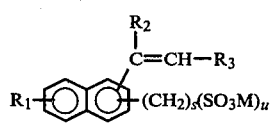
(H)

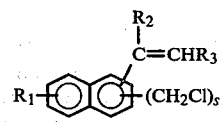
(I)

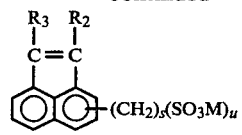
(J)

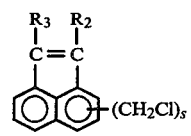
(K)

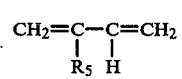
(L)

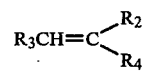
(M)

wherein the substituents $R_1$, $R_2$, $R_3$, $R_4$, and $R_5$ are as defined above for the repeating units of structures (A) to (E), r is zero or 1, s is an integer from 0 to 3, t is zero or 1, provided that when r is 1, t must be 1, and u is an integer from zero to 3 provided that when s is other than zero, u has the value of s.

Representative examples of vinylaromatic monomers, homopolymers, and copolymers which are available in commerce and can be converted to the hydrophilic polymeric sulfonates of this invention are the following:

(a) Polystyrene and sodium polystyrene sulfonate of varying molecular weights available from Pressure Chemical Company, i.e.

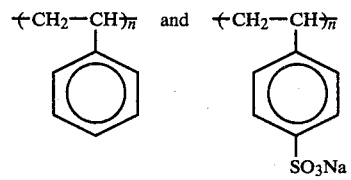

(b) Styrene/butadiene (85/15) copolymer,

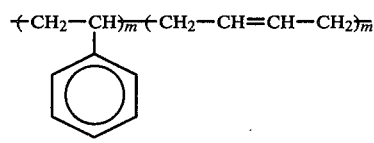

(c) Styrene/isobutylene (60/40) copolymer,

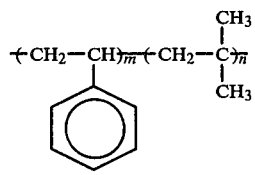

(d) Vinylbenzyl chloride monomer, 60/40 meta-/paraisomers, available from Dow Chemical Company,

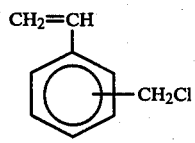

and (e) Halostyrene monomers available from Polysciences, Inc., and Aldrich Chemical Company,

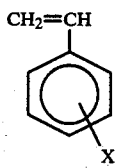

wherein X is selected from F, Cl and Br. Sulfonated homopolymers and copolymers of this invention, having repeating units of one or more of structures (A), (B), (C), (D), and (E), can be synthesized by different methods which vary mostly in how the hydrophilic sulfonic acid or sulfonic acid salt groups are introduced onto the aromatic rings. For example, in structures (A), (B), and (C), when the subscript, p, is zero so that the sulfonic acid group is bonded directly to the aromatic ring, the sulfonated polymers are synthesized by either (1) aromatic sulfonation of the respective homopolymers or copolymers (referred to hereinafter as Method 1) or (2) homopolymerization or copolymerization of sulfonic acid-substituted vinylaromatic monomers (Method 2). Examples of these two methods are shown in equations (1) and (2).

Method 1:

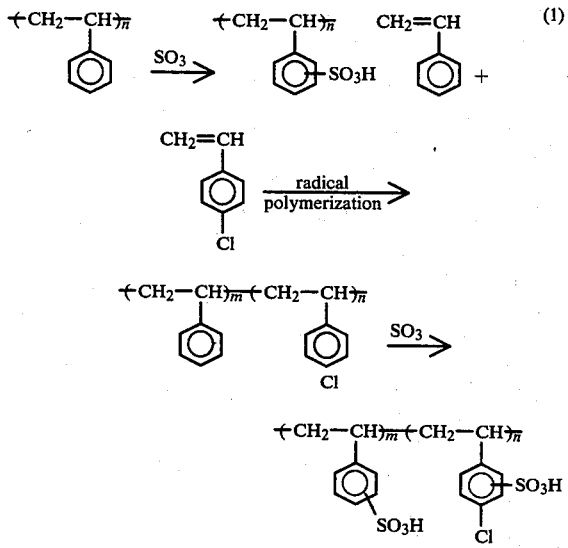

Method 2:

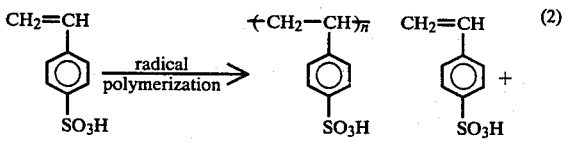

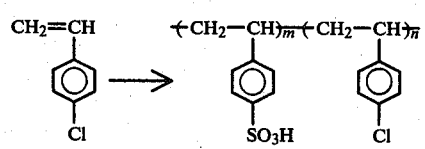

When the sulfonate group is not bonded directly to the aromatic ring, but is bonded through a methylene group ($CH_2$) i.e., when subscript p in repeating units (A), (B), and (C) is greater than zero, the sulfonate group is introduced by reaction of the corresponding chloromethyl ($CH_2Cl$)-substituted vinylaromatic monomers, homopolymers, or copolymers with sodium sulfite according to the well-known Strecker reaction (hereinafter referred to as Method 3), outlined in equation (3) and illustrated in greater detail in equations (4) and (5).

Method 3:

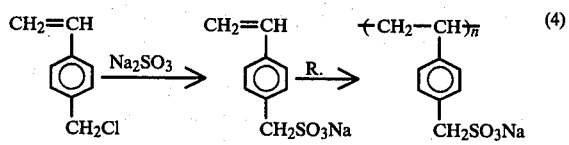

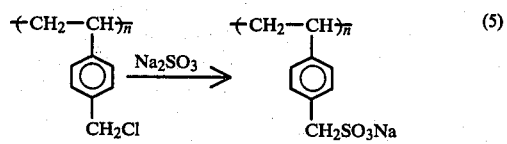

A process for conversion of chloromethylstyrene (mixed isomers) to sodium poly(vinylbenzylsulfonate) via intermediate formation of sodium vinylbenzylsulfonate monomer, in accordance with the foregoing scheme, is described in U.S. Pat. No. 2,909,508. Monomers represented by structures (F) to (K) can be homopolymerized or copolymerized with one another or with monomers (L) and (M) in various proportions, by either thermal polymerization in bulk or, preferably, free radical-catalyzed polymerization with catalysts such as benzoyl peroxide, dicumyl peroxide, potassium persulfate/sodium metabisulfite redox systems, and 2,2'-azobisisobutyronitrile (AIBN). The general polymerization procedures and techniques for isolation and purification of the resultant polymers are well known and described in such polymer texts as W. R. Sorenson and T. W. Campbell, "Preparative Methods of Polymer Chemistry," Interscience, 1961, and E. A. Collins, J. Bares, and F. W. Billmeyer, Jr., "Experiments in Polymer Science," John Wiley & Sons, 1973. As discussed above, the homopolymers and copolymers can be converted to their sulfonic acid or sulfonic acid derivatives by either aromatic sulfonation (Method 1) or by reaction of the pendant chloromethyl groups with sodium sulfite (Method 3).

Suitable sulfonation agents for preparing the sulfonated polymeric plaque barriers of this invention include anhydrous sulfur trioxide, triethyl phosphate (TEP) complexes of sulfur trioxide, and chlorosulfonic acid. Due to the high reactivity of sulfur trioxide and its potent dehydration properties, sulfonation reactions with sulfur trioxide sometimes result in formation of highly insoluble polymer dispersions due to crosslinking caused by inter-polymer chain sulfone formation. In these situations, it is preferable to moderate the sulfonation reactivity by utilization of the sulfur trioxide complexes with triethyl phosphate (TEP), which minimize or essentially eliminate formation of crosslinked by-products [cf. A. F. Turbak, Ind. Eng. Chem., Prod. R & D, 1, 275 (1962); U.S. Pat. No. 3,072,619 (Jan. 8, 1963); A. F. Turbak and A. Noshay, U.S. Pat. No. 3,206,492 (Sept. 14, 1965); N. H. Canter, U.S. Pat. No. 3,642,728 (Feb. 15, 1972); A. Noshay and L. M. Robeson, J. Applied Polymer Science, 20, 1885 (1976)].

Sulfonations are effected in solvents such as methylene chloride, 1,2-dichloroethane, and chloroform, since these are generally good solvents for the starting aromatic polymer and poor solvents for the sulfonated polymer, which often precipitated directly from the reaction medium and was filtered. In those instances where the product is soluble in the reaction medium and does not precipitate, the sulfonated polymer can be isolated by removing the solvent and converted to well-defined solids by either trituration or slurrying with an appropriate non-solvent.

Three modes of reacting the sulfonation agent and polymer were examined: (1) addition of sulfonation agent to polymer, (2) addition of polymer to the sulfonation agent, and (3) simultaneous addition of the sulfonation agent and polymer to the reaction medium. Methods (1) and (3) were preferred, since addition of the polymer to the sulfonation agent [method (2)] sometimes gave rise to non-uniform products, probably because of the large excess of sulfonation agent present during the early stages of the reaction. The most preferred sulfonation process was that of method (3), involving simultaneous additions of the reactants. These conditions afforded sulfonated products of greater uniformity and which often precipitated directly from the reaction as finely divided solids, thereby minimizing occlusion of solvent, residual acids, complexing agents (e.g., triethyl phosphate), and unreacted polymer by the sulfonated polymer.

As discussed in greater detail hereinafter, the degree of sulfonation (D.S.) also has a significant effect on the control of dental plaque deposition. D.S. as used herein is the average number of sulfonate salt or free sulfonic acid groups per aromatic ring in the polymeric structure.

Temperature control of the sulfonation reaction with sulfur trioxide and its complexes with TEP is not very critical. Acceptable results are obtained over a $-20°$ C. to $+40°$ C. range. Sulfonations are generally effected at ambient room temperatures, since the sulfonation exotherm is very mild.

Typical impurities in the sulfonated polymer are small amounts of unreacted polymer, excess sulfonation agent (as sulfuric acid), and residual triethyl phosphate which are occluded in the solid polymer. Substantial purification is effected by slurrying the polymeric sulfonic acid derivatives in non-solvents therefor, such as the halocarbons.

Removal of the free sulfuric acid is difficult, since it complexes strongly with the polymeric product. Diethyl ether is an exceptionally good complexing agent for sulfuric acid and effectively removes this contaminant when freshly isolated polymeric solids are slurried in the ether and filtered. Other effective additives for sulfuric acid removal are halocarbon solvent blends with diethyl ether and other oxygentated solvents, such as ethyl acetate and acetone. The sulfuric acid, if not removed, results in contamination of the metal salts, prepared by neutralization or ion-exchange reactions on the polymeric sulfonic acid intermediates, with considerable inorganic sulfate, such as sodium sulfate, in the case where the sodium sulfonate polymer is produced.

The preferred process for purification of the sulfonated polymers, particularly highly water soluble types, is by dialysis in membrane tubes or hollow fiber dialyzing units having a molecular weight cut-off well below the molecular weight of the polymer. Dialysis removes all of the low molecular impurities, triethyl phosphate, and inorganic salts. High purity polymers are isolated as solids by freeze-drying the dialyzed polymer solution.

The free sulfonic acid derivatives of the vinylaromatic polymers of the present invention are highly effective in reducing the deposition of plaque during in vitro testing, but these sulfonic acid polymers are too highly acidic to permit use in the oral environment unless suitably buffered. Various salts of the polymeric sulfonic acids are preferred forms of these derivatives because of increased solubility in aqueous media and lower degree of acidity. These salts exhibited good plaque barrier properties when tested in vitro.

The in vitro test procedure we have employed begins with growth of plaque in small jars containing sterilized trypticase media that has been supplemented with sucrose. Typically, ten jars are individually inoculated with 0.5 ml of unpooled freshly collected human plaque from 10 subjects. In a control series, a presterilized glass slide or an extracted human tooth is inserted into each jar. In the test series, the tooth or glass slide is pretreated with a 1% solution of the test compound (dissolved in water or other vehicle), allowed to dry in order to deposit a thin film of the compound on the surface, and the glass slide or tooth placed in the growth media. The jars are incubated under anaerobic conditions for two days at 37° C. The tooth or glass slide is removed, air dried, and stained with 0.15% FD & C #3 red dye solution to reveal the accumulated plaque deposits. The tooth or glass slide is scored for plaque density on a 0 to 5 scale. Plaque barrier activity is reported as the % of average plaque reduction, as compared to appropriate controls for ten subjects.

The degree of sulfonation of the vinylaromatic homopolymers and copolymers has a significant effect on the reduction of plaque deposition; a certain minimal D.S. is required for development of adequate plaque barrier activity. The D.S. can be varied by adjusting the conditions of the sulfonation reaction, such as the molar ratio of sulfonating agent to polymer. The nature of the aromatic polymer repeating unit governs the maximum D.S. which can be achieved. Electronic and steric effects determine the position of sulfonation as well as ease of sulfonation. These mechanistic considerations have been reviewed in general organics texts, such as that by R. T. Morrison and R. N. Boyd, "Organic Chemistry," Third Edition, Allyn and Bacon, Inc., Boston, 1973. While the exact position of the sulfonic acid and sulfonic acid salt groups on the aromatic rings is often not known with certainty, this is not considered important in the practice of this invention.

The degree of sulfonation (D.S.) of the polyvinylaromatic polymers can be determined by any of several methods: (a) NMR analysis, (b) elemental analysis for sulfur to carbon ratio, or (c) direct titration of the sulfonic acid with standard sodium hydroxide. The NMR method was perhaps the more exact procedure, since it was not prone to interference by other impurities, such as with the acidimetric or elemental analyses. Acidimetric assays for D.S. agreed well with those determined via NMR when the sulfonic acid polymer was carefully washed free of entrapped sulfuric acid and thoroughly dried and, in this regard, was often the most convenient assay method for monitoring the progress of the sulfonation reaction. Good correlation between calculated and theoretical values for the metal salt content of the sulfonated polymers, determined by atomic absorption, was obtained on polymers which were carefully purified by dialysis.

The acidimetric procedure for D.S. determination involves titration of an accurately weighed two gram sample (±0.1 mg) of the sulfonic acid polymer, dissolved in about ten volumes of water, alcohol, or other solvents, with standardized sodium hydroxide to the potentiometric endpoint. The acidity, A, of the samples is expressed in milliequivalents/gram (meq/g). Using the acidity value, A, and the formula weight, R, of the unsulfonated repeat unit in the polymer, the D.S. is calculated from the following equations:

$$A = \frac{(\text{ml. of titrant}) (\text{Normality})}{\text{sample weight, in grams}}$$

$$D.S. = \frac{(R)(A)}{1000 - 80A}$$

The alkali metal salts of the sulfonated polymers are conveniently prepared by neutralization of a water or alcohol solution of the polymeric sulfonic acid derivative with alkali metal hydroxide solutions to the potentiometric endpoint. The salts are recovered by filtration, solvent stripping, or freeze drying, depending on the type of solvent used and whether the salt precipitates directly from the solvent media. Alternatively, sulfonate salts can be prepared by addition of at least stoichiometric quantities of an alkali metal oxide, carbonate, acetate, chloride, nitrate, or sulfate to the sulfonic acid derivative. The salts either precipitate directly, or they are isolated by solvent stripping. Purification of the sulfonate salt by dialysis is the preferred procedure for the more highly water soluble salts. Multivalent metal salts of the sulfonated polymers, such as the calcium, magnesium, zinc, and aluminum salts, can be prepared by methods similar to those described above. In an alternate procedure, multivalent metal salts can be prepared by an ion-exchange reaction between the multivalent ion and either the free sulfonic acid or an alkali metal sulfonate derivative of the polymer. The neutralization and other salt forming reactions described above are essentially ion-exchange reactions, as typified by the following equations, where P represents the polymer chain:

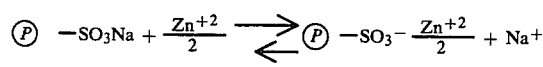

Ammonium salts of the sulfonic acid polymer can be prepared by direct addition of ammonia or a primary, secondary, or tertiary organic amine.

The plaque barrier activities of some typical sulfonated salts of vinylaromatic polymers of the invention are summarized in Tables 1–5. Generally, good plaque barrier activity is obtained only when the average number of sulfonate groups per aromatic group within the polymer is at least about 0.3. Aside from being insoluble in water, the non-sulfonated polymeric intermediates exhibit no plaque barrier properties whatsoever. Effective plaque barrier activity is seen only when the hydrophilic properties of the polymer are increased by introduction of either sulfonic acid or sulfonate salt functional groups. The molecular weight of the plaque barrier polymers is not a critical factor. In fact, useful polymers may have an average molecular weight falling within the broad range of about 500 to about 2,000,000, a more preferred range being about 2,000 to about 300,000.

TABLE 1

Plaque Barrier Activity of Sodium Polystyrene Sulfonates

| Polystyrene Molecular Weight | Degree of Sulfonation (D.S.) | % Plaque Reduction |
|---|---|---|
| 208–1,458 | 0.5 | 82 |
| 2,200 | 0.3 | 76 |
|  | 0.6 | 50–68 |
|  | 0.8 | 44 |
|  | 1.0 | 58 |
| 4,000 | 0.9 | 47 |
| 17,500 | 0.8 | 52 |
|  | 1.1 | 32 |
| 37,000 | 1.3 | 30 |
| 110,000* | 1.1 | 58 |
| 300,000 | 0.3 | 42 |
|  | 0.4 | 68 |
|  | 0.5 | 58–65 |
|  | 0.7 | 58 |
|  | 0.8 | 38–44 |
| 321,000 | 1.1 | 40 |

*Dicarboxyl terminated polystyrene, Aldrich Chemical Co.

TABLE 2

Plaque Barrier Activity of Substituted Polystyrene Sodium Sulfonates

| Polymer of | D.S. | % Plaque Reduction |
|---|---|---|
| vinyltoluene | 0.3 | 78 |
|  | 0.6 | 44 |
|  | 1.1 | 44 |
| 4-t-butylstyrene | 0.4 | 27 |
| 4-fluorostyrene | 0.5 | 71 |
| 2-chlorostyrene | 0.6 | 87 |
|  | 1.1 | 90 |
| 3-chlorostyrene | 0.7 | 95 |
| 4-chlorostyrene | 0.5 | 60–94 |
|  | 1.2 | 66 |
| chlorostyrenes, mixed isomers* | 0.4 | 20 |
|  | 0.5 | 78–89 |
|  | 0.6 | 76 |
|  | 0.8 | 78 |
|  | 1.2 | 76 |
| 4-bromostyrene | 0.4 | 2 |
|  | 0.7 | 68 |
| 4-vinylanisole | 0.9 | 69 |
| α-methylstyrene | 0.6 | 12 |
|  | 0.8 | 50 |
|  | 1.2 | 44 |
| anethole | 0.9 | 36 |
|  | 1.0 | 24 |

*60/40 mixture of ortho- and para- isomers; viscosity average molecular weight of 139,000

TABLE 3

Plaque Barrier Activity of Sodium Sulfonate Derivatives of Styrene Copolymers

| Copolymer Composition, mole % | D.S. | % Plaque Reduction |
|---|---|---|
| 84% styrene/ 16% 4-chlorostyrene | 0.6 | 40 |

TABLE 3-continued

Plaque Barrier Activity of Sodium Sulfonate Derivatives of Styrene Copolymers

| Copolymer Composition, mole % | D.S. | % Plaque Reduction |
|---|---|---|
| 66% styrene/ | 0.6 | 50 |
| 34% 4-chlorostyrene | | |
| 47% styrene/ | 0.4 | 69 |
| 53% 4-chlorostyrene | 0.6 | 60 |
| | 0.8 | 73 |
| 85% styrene/ | 1.0 | 36 |
| 15% butadiene | | |
| 60% styrene/ | 0.6 | 42 |
| 40% isobutylene | 0.8 | 38 |

TABLE 4

Plaque Barrier Activity of Metal Salts of Poly(60/40 m,p-vinylbenzylsulfonic acid)

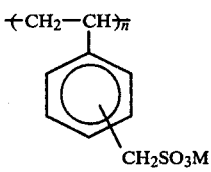

| Metal Salt, M | % Plaque Reduction |
|---|---|
| Sodium | 70–89 |
| Zinc | 90 |
| Aluminum | 80 |

TABLE 5

Plaque Barrier Activity of Poly(Vinylnaphthalene) and Poly(Acenaphthylene) Sodium Sulfonates

| Polymer of | D.S./ring | % Plaque Reduction |
|---|---|---|
| 1-Vinylnaphthalene | 0.5 | 84 |
| | 0.9 | 46–52 |
| 2-Vinylnaphthalene | 0.3 | 8 |
| | 0.7 | 44 |
| | 0.8 | 62–74 |
| | 0.9 | 68 |
| | 1.2 | 58 |
| Acenaphthylene | 0.7 | 40 |
| | 1.6 | 68 |
| | 2.6 | 50 |

EXAMPLE 1

Sodium Polystyrene Sulfonate, D.S. 0.6

A solution of 1.0 g polystyrene, MW 2200 (Pressure Chemical Co.), in 45 ml. dry methylene chloride was prepared. With stirring and under a slight positive pressure, a solution of 1.0 g. liquid sulfur trioxide in 15 ml. methylene chloride was added over 15 minutes at 2°–7° C. After stirring another 10 minutes at 0°–5° C., the filtered reaction mixture was solvent stripped and the residual gum triturated with ether several times and dried. The yield of polystyrene sulfuric acid, a beige-colored powder, was 1.6 g. Titration of an accurately weighed sample with sodium hydroxide in methanol as solvent to the neutralization endpoint indicated a sulfonic acid functionality of 3.70 meq/g, equivalent to a D.S. of 0.6. Removal of the solvent from the neutralized solution gave the sodium polystyrene sulfonate derivative as off-white solids.

EXAMPLE 2

Zinc Polystyrene Sulfonate, D.S. 1.0

To a solution of 2.3 g. (0.0112 equiv.) sodium polystyrene sulfonate, D.S. 1.0 (Pressure Chemical Co.), in 25 ml. water was added a solution of 1.5 g. (0.0224 equiv.) zinc chloride in 10 ml. water. After standing 30 minutes, the solution was transferred to a Spectropor 6 membrane tube (MW 2000 cutoff) and dialyzed in distilled water for 24 hours. The dialyzed polymer solution was freeze-dried to give 2.3 g. of zinc polystyrene sulfonate, D.S. 1.0, as white solids. Analysis: Zinc. 12.5%; sodium, 0.12%.

EXAMPLE 3

Styrene/4-Chlorostyrene Copolymer (47/53)

A solution of 13.9 g. 4-chlorostyrene and 10.4 g. styrene in 120 ml. dry benzene containing 0.24 g. azobisisobutyronitrile (Vazo ® 64, du Pont) was stirred under nitrogen at 58°–64° C. for 24 hours. The solution was solvent stripped to a colorless syrupy residue which was dissolved in 50 ml. benzene and the solution added slowly with stirring to 300 ml. absolute ethanol. The precipitated polymer was filtered, washed with ethanol, and dried. The yield was 15.2 g. Analysis of the polymer showed presence of 15.83% chlorine, equivalent to a copolymer containing 47 mole % styrene and 53 mole % 4-chlorostyrene units in the repeat unit.

EXAMPLE 4

Sulfonation of 47/53 Styrene/4-Chlorostyrene Copolymer

A solution of 1.96 g. liquid sulfur trioxide in 25 ml. methylene chloride containing 1.5 g. of triethyl phosphate was prepared and added over 8 minutes at 24°–31° C. to a stirred solution of 3.0 g. of the 47/53 styrene/4-chlorostyrene copolymer (Example 3) dissolved in 30 ml. methylene chloride. After stirring an additional 20 minutes at 30° to 27° C., the suspension of finely divided solids were solvent stripped and the residual solids slurried in 100 ml. ether and filtered. The yield of the sulfonic acid derivative of the copolymer was 4.0 g.

A solution of 2.9866 g. of the polymeric sulfonic acid in 60 ml. methanol was neutralized from pH 0.2 to pH 9.1 by addition of 13.2 ml. 0.556 N methanolic sodium hydroxide. The neutralized solution was stripped free of solvent to afford 2.9 g. of the sodium sulfonate salt of the copolymer. Based on the titer, the D.S. was 0.4.

EXAMPLE 5

Sodium poly(m,p-vinylbenzylsulfonate)

A mixture consisting of 15.3 g (0.100 mole) m,p-vinylbenzyl chloride monomer (60/40 meta/para isomers; Dow Chemical), 25.2 g. (0.200 mole) sodium sulfite, and 100 ml. water was stirred vigorously at reflux for 5 hours. The cooled solution was gravity filtered to remove a small amount of solids and the filtrate extracted with 3×50 ml. methylene chloride to remove any residual monomer. The aqueous phase was placed in a Spectropor 6 dialysis membrane tube (MW 2000 cutoff) and dialyzed in water for several days. The dialyzed polymer solution was concentrated in vacuo to glassy, colorless solids. The yield of sodium poly(m,p-vinylbenzylsulfonate) was 20.0 g.

EXAMPLE 6

Sulfonation of Poly(2-vinylnaphthalene)

A sulfonation mixture, consisting of 1.68 g. (0.021 mole) liquid sulfur trioxide dissolved in a solution of 1.27 g. (0.007 mole) triethyl phosphate in 42 ml. methylene chloride, was added over 5 minutes at $-9°$ to $-3°$ C. to a stirred solution of 2.31 g. (0.015 mer units) poly(2-vinylnaphthalene) in 30 ml. methylene chloride. The suspension was allowed to warm from $-5°$ C. to $+20°$ C. over 30 minutes and the solids filtered, washed with methylene chloride and ether, and dried to afford 3.4 g. of poly(2-vinylnaphthalene) sulfonic acid, a tan powder of D.S. 0.8.

The plaque barrier oral compositions of this invention may comprise any conventional pharmaceutically acceptable oral hygiene formulation that contains (and is compatible with) an effective amount of a plaque barrier agent as defined herein. Such formulations include, for example, mouthwashes, rinses, irrigating solutions, abrasive and nonabrasive gel dentifrices, denture cleansers, coated dental floss and interdental stimulator coatings, chewing gums, lozenges, breath fresheners, foams and sprays.

The plaque barrier agents may be present in these formulations in effective concentrations generally in the range of from about 0.05 weight percent to as much as 30 weight percent or the limit of compatibility with the vehicle. However, no advantage will be derived from concentrations in excess of about 20 weight percent. A preferred concentration range for the plaque barrier agents in the formulations of the invention is from about 0.5 to about 10 weight percent. A more preferred range is from about 2 to about 8 percent by weight, about 5% being the presently most preferred concentration in a nonabrasive gel vehicle.

The pH of these plaque barrier preparations should be between pH 5.0 and 10.0, preferably between pH 5.0 and 8.0, more preferably between about pH 6.0 and 7.5. Lower pH than 5.0 is undesirable because of the possible enhancement of enamel demineralization.

Suitable conventional pharmaceutically acceptable vehicles that can be employed with the plaque barrier agents to prepare the barrier compositions of this invention may comprise water, ethanol; such humectants as polypropylene glycol, glycerol and sorbitol; such gelling agents as cellulose derivatives, for example, Methocel, carboxymethylcellulose (CMC 7MF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidial magnesium aluminosilicate complexes such as Veegum, and mucoprotein thickening agents such as Carbopol 934; gel stabilizers such as the silicon dioxides, for example, Cab-O-Sil M5, and polyvinylpyrrolidone; sweeteners such as sodium saccharin; preservatives such as citric acid, sodium benzoate, cetylpyridinium chloride, potassium sorbate, methyl and ethyl parabens; detergents such as sodium lauryl sulfate, sodium cocomonoglyceride sulfonate, sodium lauryl sarcosinate and polyoxyethylene isohexadecyl ether (Arlasolve 200) and approved colors and flavors. The following specific examples will serve further to illustrate the plaque barrier compositions of this invention.

EXAMPLE A—Mouthwash Solution

| | |
|---|---|
| Barrier Agent | 0.5-2.0 % w/w |
| Glycerol (humectant) | 6.0 |
| Pluronic F-108 | 1.0 |
| Sodium saccharin (sweetener) | 0.3 |
| Deionized Water | q.s. |
| Flavors | 1.0 |
| | 100.0 |

EXAMPLE B—Mouthwash Solution

| | |
|---|---|
| Plaque Barrier Agent | 0.5-3.0 % w/w |
| Ethanol, USP | 15.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |
| | 100.0 |

EXAMPLE C—Abrasive Dentrifice Gel

| | |
|---|---|
| Plaque Barrier Agent | 2.0-10.0 % w/w |
| Fumed Silica (abrasive) | 55.0 |
| Sodium Lauryl Sulfate (detergent) | 1.5 |
| Glycerol (humectant) | 10.0 |
| Carboxymethylcellulose (gelling agent) | 2.0 |
| Sodium saccharin (sweetener) | 0.2 |
| Sorbitol (humectant) | 10.0 |
| Flavors | 1.0 |
| Deionized Water | q.s. |
| Preservative | 0.05 |
| | 100.0 |

EXAMPLE D—Chewing Gum

| | |
|---|---|
| Plaque Barrier Agent | 1.0-11.0 % w/w |
| Gum Base | 21.3 |
| Sugar | 48.5-58.5 |
| Corn Syrup (Baume 45) | 18.2 |
| Flavors | 1.0 |
| | 100.0 |

EXAMPLE E—Nonabrasive Gel Dentifrice

| | |
|---|---|
| Plaque Barrier Agent | 0.05-30.0 % w/w |
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium Saccharin | 0.2 |
| Flavors | 1.5 |
| | 100.0 |

EXAMPLE F

The following formulation illustrates a presently preferred nonabrasive gel composition containing a barrier agent in accordance with the present invention.

| Ingredients | % w/w |
|---|---|
| Distilled Water | q.s. |

-continued

| Ingredients | % w/w |
|---|---|
| Sodium Saccharin (sweetener) | 0.20 |
| Sodium Benzoate (preservative) | 0.30 |
| FD&C Blue #1 (0.1% aq. soln.) | 0.27 |
| D&C Yellow #10 (0.5% aq. soln.) | 0.50 |
| Gelling agent | 18.00 |
| Glycerol (Humectant) | 20.00 |
| Cab-O-Sil M5 (Silicon Dioxide) | 1.00 |
| Plaque Barrier Agent | 5.00 (dry basis) |
| Flavor | 0.80 |
| | 100.0 |

While the details of preparing all of the above formulations are well within the skill of the art, a suggested procedure for preparing the gel formulation of this example will be described for completeness.

In a first container the water, sodium saccharin, sodium benzoate and dyes are mixed. Then the container is put into an ice bath. When the temperature reaches 6° C., the gelling agent is added and the contents mixed slowly until the gelling agent is dissolved. Then the solution is heated to 70° C.

Into a second container is added the glycerin. Then the Cab-O-Sil M5 is sprinkled in with mixing. Then the plaque barrier agent is added and mixing continued to a smooth paste. The paste is then heated in a water bath with mixing to a temperature of 70° C.

The contents of the first container are added to the second container and blended together until the batch is homogeneous while maintaining a 70° C. temperature. Then the flavoring is added, all mixing is stopped, and the formulation allowed to settle for approximately one hour. If necessary to remove air bubbles, overnight refrigeration may be employed.

While any pharmaceutically acceptable gelling agent that is compatible with the plaque barrier agent may be employed, a presently preferred gelling agent is Pluronic F-127.

These compositions are preferably employed from one to three times daily in a routine oral hygiene program to prevent the attachment of plaque to the teeth.

Variations can, of course, be made without departing from the spirit or scope of the invention.

We claim:

1. An oral hygiene composition comprising an effective amount for preventing deposition of dental plaque on teeth of a sulfonated vinylaromatic polymer of at least 50% by weight of at least one repeating unit selected from the group consisting of structure (A),

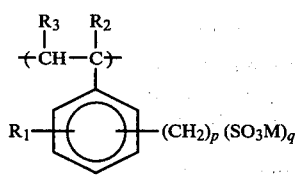

structure (B),

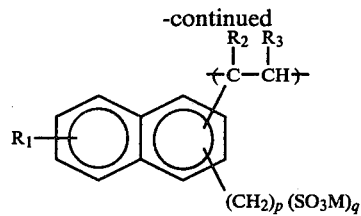

and structure (C),

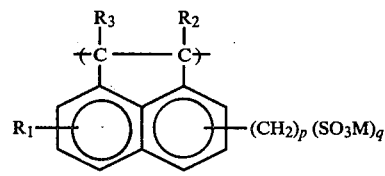

and from 0 to 50% by weight of a repeating unit selected from the group consisting of structure (D),

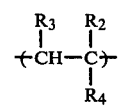

and structure (E),

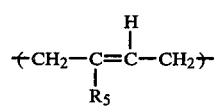

wherein $R_1$ is selected from the group consisting of hydrogen, linear or branched lower alkyl of up to 5 carbon atoms, alkoxy of 1–20 carbon atoms, fluorine, chlorine, and bromine; $R_2$ and $R_3$ are each independently selected from the group consisting of hydrogen and methyl; $R_4$ is hydrogen or an alkyl group of 1–18 carbon atoms; and $R_5$ is selected from the group consisting of hydrogen, methyl, chlorine, bromine, and phenyl, q, which is the average number of sulfonate groups per aromatic groups, has a value in the range of from about 0.3 to about 2.6, p is either zero or a number equal to the value of q, M is selected from the group consisting of lithium, sodium, potassium, calcium, magnesium, zinc, aluminum, hydrogen and the ammonium salt derived from ammonia or a pharmaceutically-acceptable organic amine, said polymer having an average molecular weight in the range of about 500 to about 2,000,000 in a pharmaceutically-acceptable oral hygiene vehicle compatible with said polymer.

2. The composition of claim 1 wherein said polymer consists essentially of repeating units of structure A, and q has a value in the range of from about 0.3 to about 1.0.

3. The composition of claim 1 wherein said polymer consists essentially of repeating units selected from the group consisting of structure B and structure C, and q has a value in the range of about 0.5 to about 2.6.

4. The composition of claim 1 wherein M is a metal selected from the group consisting of potassium, lithium, sodium, calcium, magnesium, zinc and aluminum.

5. A method of preventing deposition of dental plaque on teeth comprising periodically applying to the teeth a composition of claim 1.

6. The method of claim 5 wherein said composition is applied from about 1 to about 3 times per day.

7. The composition of claim 1 in the form of an oral hygiene formulation selected from the group consisting of mouthwashes, mouthrinses, irrigating solutions, abrasive gel dentifrices, non-abrasive gel dentifrices, denture cleansers, coated dental floss, coated interdental stimulators, chewing gums, lozenges, breath fresheners, foams and sprays.

* * * * *